(12) United States Patent
He et al.

(10) Patent No.: US 11,883,211 B2
(45) Date of Patent: Jan. 30, 2024

(54) RESPIRATORY MODELING USING DEEP LEARNING FOR MR IMAGING WITH PILOT TONE NAVIGATION

(71) Applicant: Siemens Healthcare GmbH, Erlangen (DE)

(72) Inventors: Jin Qiang He, Shenzhen (CN); Fang Dong, Shenzhen (CN); De He Weng, Shenzhen (CN)

(73) Assignee: Siemens Healthcare GmbH, Erlangen (DE)

( * ) Notice: Subject to any disclaimer, the term of this patent is extended or adjusted under 35 U.S.C. 154(b) by 88 days.

(21) Appl. No.: 17/338,099

(22) Filed: Jun. 3, 2021

(65) Prior Publication Data

US 2021/0378603 A1 Dec. 9, 2021

(30) Foreign Application Priority Data

Jun. 4, 2020 (CN) .......................... 202010498877.3

(51) Int. Cl.
*A61B 5/00* (2006.01)
*A61B 5/08* (2006.01)
*A61B 5/055* (2006.01)

(52) U.S. Cl.
CPC ............ *A61B 5/7292* (2013.01); *A61B 5/055* (2013.01); *A61B 5/0816* (2013.01); *A61B 5/7267* (2013.01)

(58) Field of Classification Search
None
See application file for complete search history.

(56) References Cited

U.S. PATENT DOCUMENTS

| 6,937,696 B1* | 8/2005 | Mostafavi | A61B 5/113 378/65 |
| 2011/0116695 A1* | 5/2011 | Wollenweber | G06T 7/20 382/131 |
| 2017/0202533 A1* | 7/2017 | Wollenweber | A61B 6/037 |

OTHER PUBLICATIONS

Lee, Suk Jin, "Prediction of Respiratory Motion," (May 2012), Virginia Commonwealth University, thesis, retrieved from <https://scholarscompass.vcu.edu/etd/336/> on Sep. 15, 2022. (Year: 2012).*

(Continued)

*Primary Examiner* — Joel Lamprecht
*Assistant Examiner* — Ashish S Jasani
(74) *Attorney, Agent, or Firm* — Banner & Witcoff Ltd.

(57) ABSTRACT

The disclosure relates to techniques for triggering magnetic resonance data acquisition. The techniques include detecting a respiration direction of a respiration signal of an acquisition subject, predicting in real time an amplitude peak value of an expiration signal in the current respiration period according to the real-time respiration signal of the acquisition subject, multiplying the amplitude peak value by a preset coefficient, and using the product as a trigger point threshold of the current respiration period. When it is determined that an expiration stage of the current respiration period is starting, the techniques also include calculating in real time or periodically the absolute value of the difference between the amplitude of the current expiration signal and the trigger point threshold currently calculated, and if the absolute value of the difference is less than a preset difference threshold, then triggering MR data acquisition.

10 Claims, 7 Drawing Sheets

(56) References Cited

OTHER PUBLICATIONS

Nobavi et al., "Respiratory Motion Prediction Using Deep Convolutional Long Short-Term Memory Network," (Apr. 25, 2020), Journal of Medical Signals & Sensors, 10(2): 69-75. (Year: 2020).*
Lv et al., "Respiratory motion correction for free-breathing 3D abdominal MRI using CNN-based image registration: a feasibility study," (Jan. 31, 2018), Br J Radiol.; 91(1083): 20170788. (Year: 2018).*
Lin et al "Towards Real-Time Respiratory Motion Prediction based on Long Short-Term Memory Neural Networks," (Apr. 10, 2019), Phys. Med. Biol. 64 085010. (Year: 2019).*
Lee et al., "Prediction and Classification of Respiratory Motion," (Oct. 25, 2013) Studies in Computational Intelligence (SCI, vol. 525). (Year: 2013).*
Lenk, Mary, "Respiratory Motion Tracking in Magnetic Resonance Imaging with Pilot Tone Technology," (Jul. 17, 2018) Master of Science, Ohio State University, Electrical and Computer Engineering, <https://etd.ohiolink.edu/apexprod/rws_olink/r/1501/10?clear=10&p10_accession_num=osu1531838630931375>. (Year: 2018).*

* cited by examiner

131: Respiration direction detection module

132: Expiration peak value prediction module

133: Triggering detection module

134: Respiration direction detection model establishing module

135: Expiration peak value predictive model establishing module

136: Respiration signal prediction module

137: Respiration signal predictive model establishing module

Fig. 14

RESPIRATORY MODELING USING DEEP LEARNING FOR MR IMAGING WITH PILOT TONE NAVIGATION

CROSS-REFERENCE TO RELATED APPLICATIONS

The present application claims the benefit of the filing date of China patent application no. CN 202010498877.3, filed on Jun. 4, 2020, the contents of which are incorporated herein by reference in their entirety.

TECHNICAL FIELD

The disclosure relates to MRI (magnetic resonance imaging), and in particular to a method and apparatus for triggering MR (magnetic resonance) data acquisition, and a readable storage medium.

BACKGROUND

In MRI, a radio frequency (RF) pulse of a specific frequency is applied to a human body in a static magnetic field, such that hydrogen protons in the human body are excited and experience the phenomenon of MR. When the pulse is stopped, the protons give rise to MR signals in the course of relaxation. An MR image is created by processing including MR signal reception, spatial encoding and image reconstruction.

Breathing movements of a patient will lower the quality of MR images for abdomen diagnosis, and this is still one of the principal challenges encountered in MR imaging diagnosis. In order to obtain an artefact-free image of the chest or abdomen, a respiration sensor is used to extract a respiration signal as a trigger signal for MR data acquisition. A pilot tone sensor is one type of sensor.

Certain problems are associated with pilot tone navigation. Firstly, pilot tone signal reception takes place at the same time as MR data acquisition, and will inevitably suffer serious interference from other events such as RF pulses or gradient pulses. In addition, the positions of the conversion coil and receiving coil relative to the patient's body are not fixed, and therefore the pilot signals generated will vary from patient to patient. In order to determine the correct trigger point, it is necessary to eliminate interference and identify different respiration phases on the basis of signal values of the respiration signal.

The optimal data acquisition window for MR imaging should be the stage in which expiration ends, because respiratory motion is smallest in this interval, and therefore in principle, fewer motion artefacts are generated.

Real-time detection of the trigger point is of key importance in methods for triggering the acquisition of MR data. However, the characteristics and modes of respiratory motion vary due to differences in time and from person to person, therefore the prediction of respiratory signal evolution is challenging, and so it is very difficult to decide when to initiate MR data acquisition; this problem has not yet been fully solved. At present, the most prevalent method is to define an amplitude threshold in advance according to several previous respiration periods, and use this amplitude threshold for judging a trigger point decision for a subsequent real-time respiration signal.

SUMMARY

In order to solve the abovementioned problem, the present disclosure provides a method for triggering MR data acquisition, to improve the accuracy of triggering of MR data acquisition;

the present disclosure also provides an apparatus for triggering MR data acquisition, to improve the accuracy of triggering of MR data acquisition;

the present disclosure also provides a readable storage medium, to improve the accuracy of triggering of MR data acquisition.

To achieve the abovementioned objective, the present disclosure provides the following technical solution:

A method for triggering magnetic resonance (MR) data acquisition, comprising:

detecting a respiration direction of a respiration signal of an acquisition subject;

predicting in real time an expiration amplitude peak value of an expiration signal in the current respiration period according to the respiration signal of the acquisition subject;

when it is determined according to the respiration direction of the respiration signal that an expiration stage of the current respiration period is starting, calculating in real time or periodically the product of the current expiration amplitude peak value and a preset coefficient to obtain a trigger point threshold of the current respiration period, calculating the absolute value of the difference between the amplitude of the current expiration signal and the trigger point threshold of the current respiration period, and if the absolute value of the difference is less than a preset difference threshold, then triggering MR data acquisition.

Before the step of detecting a respiration direction of a respiration signal of an acquisition subject, the method further comprises:

acquiring respiration signals of the same person in different time periods, and/or respiration signals of different people in the same time period or different time periods, and using the acquired respiration signals as training samples; sequentially inputting the acquired training samples into a first neural network to be trained, an output of the first neural network being a correspondence between a respiration direction and amplitude variation of the currently inputted respiration signal; and completing training to obtain a respiration direction detection model;

the step of detecting a respiration direction of a respiration signal of an acquisition subject comprises:

inputting the respiration signal of the acquisition subject into the respiration direction detection model, and determining, according to an output of the model, a correspondence between a respiration direction and amplitude variation of the respiration signal of the acquisition subject in each respiration period.

Before the step of detecting a respiration direction of a respiration signal of an acquisition subject, the method further comprises:

acquiring respiration signals of the same person in different time periods, and/or respiration signals of different people in the same time period or different time periods, and using the acquired respiration signals as training samples; sequentially inputting the training samples into a third neural network to be trained, an output of the third neural network being: an expiration amplitude peak value of the respiration period where the currently inputted respiration signal is situated; and completing training to obtain an expiration peak value predictive model, wherein a rising amplitude stage of the respiration signal in each respiration period of the training sample is expiration;

the step of predicting in real time an expiration amplitude peak value of an expiration signal in the current respiration period comprises:

inputting the respiration signal of the acquisition subject into the expiration peak value predictive model, an output of the model being an expiration amplitude peak value of the respiration period where the currently inputted respiration signal is situated, wherein the respiration signal of the acquisition subject satisfies: a rising amplitude stage of the respiration signal in each respiration period is expiration.

After the step of detecting a respiration direction of a respiration signal of an acquisition subject, but before the step of predicting in real time an expiration amplitude peak value of an expiration signal in the current respiration period, the method further comprises:

predicting in real time, according to the most recent respiration signal of a preset length of the acquisition subject, a respiration signal at the next sampling point of the acquisition subject;

moreover, the step of predicting in real time an expiration amplitude peak value of an expiration signal in the current respiration period is specifically:

predicting in real time an expiration amplitude peak value of an expiration signal in the current respiration period according to the respiration signal predicted in real time.

Before the step of detecting a respiration direction of a respiration signal of an acquisition subject, the method further comprises:

acquiring respiration signals of the same person in different time periods, and/or respiration signals of different people in the same time period or different time periods, and using the acquired respiration signals as training samples; sequentially inputting the training samples into a second neural network to be trained, an output of the second neural network being: a respiration signal at the next sampling point of the currently inputted respiration signal; and completing training to obtain a respiration signal predictive model, wherein a rising amplitude stage of the respiration signal in each respiration period of the training sample is expiration;

the step of predicting in real time, according to the most recent respiration signal of a preset length of the acquisition subject, a respiration signal at the next sampling point of the acquisition subject, comprises:

inputting the respiration signal of the acquisition subject into the respiration signal predictive model, an output of the model being a respiration signal at the next sampling point of the currently inputted respiration signal, wherein the respiration signal of the acquisition subject satisfies: a rising amplitude stage of the respiration signal in each respiration period is expiration.

The neural network is a Temporal Convolutional Network (TCN), a Recurrent Neural Network (RNN) or a Long-Short-Term-Memory (LSTM) neural network.

An apparatus for triggering magnetic resonance (MR) data acquisition, comprising:

a respiration direction detection module (e.g. circuitry), for detecting a respiration direction of a respiration signal of an acquisition subject;

an expiration peak value prediction module (e.g. circuitry), for predicting in real time an expiration amplitude peak value of an expiration signal in the current respiration period according to the respiration signal of the acquisition subject;

a triggering detection module (e.g. circuitry), for calculating in real time or periodically the product of the current expiration amplitude peak value predicted by the expiration peak value prediction module and a preset coefficient, when it is determined according to the respiration direction of the respiration signal detected by the respiration direction detection module that an expiration stage of the current respiration period is starting, to obtain a trigger point threshold of the current respiration period, calculating the absolute value of the difference between the amplitude of the current expiration signal and the trigger point threshold of the current respiration period, and if the absolute value of the difference is less than a preset difference threshold, then triggering MR data acquisition.

The apparatus further comprises:

a respiration direction detection model establishing module (e.g. circuitry), for acquiring respiration signals of the same person in different time periods, and/or respiration signals of different people in the same time period or different time periods, and using the acquired respiration signals as training samples; sequentially inputting the acquired training samples into a first neural network to be trained, an output of the first neural network being a correspondence between a respiration direction and amplitude variation of the currently inputted respiration signal; and completing training to obtain a respiration direction detection model;

moreover, the respiration direction detection module (e.g. circuitry) is specifically configured to input the respiration signal of the acquisition subject into the respiration direction detection model established by the respiration direction detection model establishing module (e.g. circuitry), and determine, according to an output of the model, a correspondence between a respiration direction and amplitude variation of the respiration signal of the acquisition subject in each respiration period.

The apparatus further comprises:

an expiration peak value predictive model establishing module (e.g. circuitry), for acquiring respiration signals of the same person in different time periods, and/or respiration signals of different people in the same time period or different time periods, and using the acquired respiration signals as training samples; sequentially inputting the training samples into a third neural network to be trained, an output of the third neural network being: an expiration amplitude peak value of the respiration period where the currently inputted respiration signal is situated; and completing training to obtain an expiration peak value predictive model, wherein a rising amplitude stage of the respiration signal in each respiration period of the training sample is expiration;

moreover, the expiration peak value prediction module (e.g. circuitry) is specifically configured to input the respiration signal of the acquisition subject into the expiration peak value predictive model established by the expiration peak value predictive model establishing module (e.g. circuitry), an output of the model being an expiration amplitude peak value of the respiration period where the currently inputted respiration signal is situated, wherein the respiration signal of the acquisition subject satisfies: a rising amplitude stage of the respiration signal in each respiration period is expiration.

The apparatus further comprises:

a respiration signal prediction module (e.g. circuitry), for predicting in real time, according to the most recent respiration signal of a preset length of the acquisition subject, a respiration signal at the next sampling point of the acquisition subject;

moreover, the expiration peak value prediction module (e.g. circuitry) is specifically configured to predict in real time an expiration amplitude peak value of an expiration signal in the current respiration period according to the respiration signal predicted in real time by the respiration signal prediction module.

The apparatus further comprises:

a respiration signal predictive model establishing module (e.g. circuitry), for acquiring respiration signals of the same person in different time periods, and/or respiration signals of different people in the same time period or different time periods, and using the acquired respiration signals as training samples; sequentially inputting the training samples into a second neural network to be trained, an output of the second neural network being: a respiration signal at the next sampling point of the currently inputted respiration signal; and completing training to obtain a respiration signal predictive model, wherein a rising amplitude stage of the respiration signal in each respiration period of the training sample is expiration;

moreover, the respiration signal prediction module (e.g. circuitry) is specifically configured to input the respiration signal of the acquisition subject into the respiration signal predictive model established by the respiration signal predictive model establishing module, an output of the model being a respiration signal at the next sampling point of the currently inputted respiration signal, wherein the respiration signal of the acquisition subject satisfies: a rising amplitude stage of the respiration signal in each respiration period is expiration.

A readable storage medium (e.g. a non-transitory computer-readable medium), having a computer program stored thereon, wherein when executed by a processor, the computer program realizes a step of any one of the methods described above for triggering magnetic resonance (MR) data acquisition.

An apparatus for triggering magnetic resonance (MR) data acquisition, wherein the apparatus comprises: a processor and a memory;

an application program executable by the processor is stored in the memory, and configured to cause the processor to perform a step of any one of the methods described above for triggering magnetic resonance (MR) data acquisition.

In the present disclosure, the amplitude peak value of the expiration signal in the current respiration period is predicted in real time according to the respiration signal of the acquisition subject, and the current trigger point threshold is determined according to the amplitude peak value, thus the trigger point threshold can vary as the amplitude of the respiration signal varies, thereby reducing the probability of missed, premature or late triggering of MR data acquisition, and increasing the accuracy of triggering of MR data acquisition.

KEY TO THE DRAWINGS

| Label | Meaning |
|---|---|
| 201-203 | steps |
| 401-403 | steps |
| 501-503 | steps |
| 801-803 | steps |
| 1001-1003 | steps |
| 1201-1210 | steps |
| 130 | apparatus for triggering MR data acquisition provided in an embodiment of the present disclosure |
| 131 | respiration direction detection module |

-continued

| Label | Meaning |
| --- | --- |
| 132 | expiration peak value prediction module |
| 133 | triggering detection module |
| 134 | respiration direction detection model establishing module |
| 135 | expiration peak value predictive model establishing module |
| 136 | respiration signal prediction module |
| 137 | respiration signal predictive model establishing module |
| 140 | apparatus for triggering MR data acquisition provided in another embodiment of the present disclosure |
| 141 | processor |
| 142 | memory |

DETAILED DESCRIPTION

To clarify the objective, technical solution, and advantages of the present disclosure, the technical solution of the present disclosure is explained in detail below on the basis of embodiments with reference to the accompanying drawings.

For example, "a" and "the" in the singular form used in the description of the present disclosure and the attached claims are also intended to include the plural form, unless clearly specified otherwise herein.

The existing techniques for determining a trigger point for MR data acquisition have the following deficiencies:

In the existing techniques, an expiration amplitude peak value is defined in advance on the basis of several previous respiration periods, e.g. at the position of straight line X in FIG. 1, and 80% of the expiration amplitude peak value is taken to be a trigger point threshold, e.g. at the position of straight line Y in FIG. 1; subsequently, in an expiration stage of each respiration period, the absolute value of the difference between the amplitude of the current expiration signal and the trigger point threshold is calculated once at intervals of a certain time period, and if the absolute value of the difference is less than a preset difference threshold, MR data acquisition is triggered.

Figure 1:
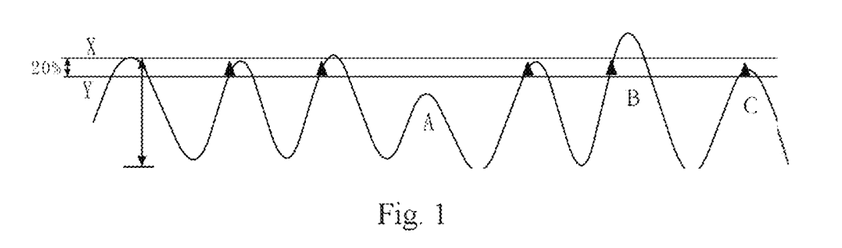
FIG. 1 is a schematic diagram illustrating an existing method to detect a trigger point for MR data acquisition.

FIG. 1 is a schematic diagram of using the existing technique to detect the trigger point for MR data acquisition; as can be seen from FIG. 1, there are cases of missed, premature, or late triggering. Specifically:

1) Missed Triggering

An example is respiration period A in FIG. 1; an expiration endpoint is essentially present in A, so MR data acquisition should be triggered, but the amplitude of the respiration signal in respiration period A is too small, and consequently the amplitude peak value of the respiration signal in this respiration period fails to reach the trigger point threshold, so no trigger point can be detected in this respiration period.

2) Premature or Late Triggering

An example is respiration period B in FIG. 1; since the amplitude of the respiration signal in respiration period B is higher, the amplitude of the respiration signal in this respiration period will reach the trigger point threshold before the end of expiration, so the trigger point is detected too early.

Another example is respiration period C in FIG. 1; since the amplitude of the respiration signal in respiration period C is lower, the amplitude of the respiration signal in this respiration period will reach the trigger point threshold after the end of expiration, so the trigger point is detected too late.

Missed detection of the trigger point will prolong the process of MR data acquisition; premature or late detection of the trigger point will result in motion artifacts in the MR image.

Figure 2:
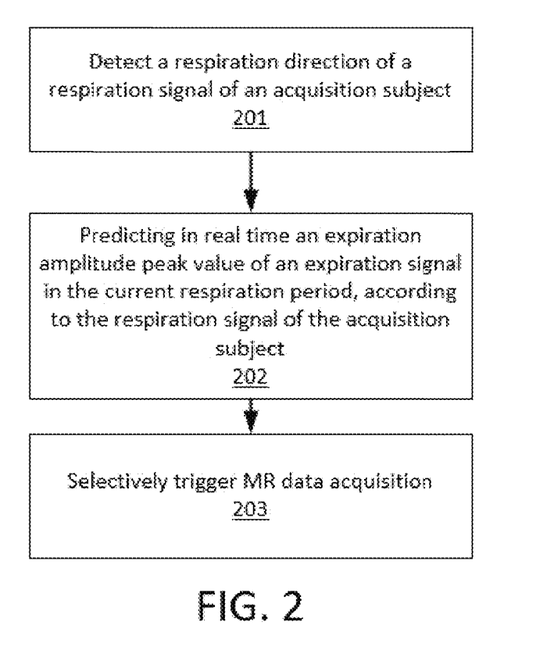
FIG. 2 is a flow chart for triggering MR data acquisition provided in accordance with embodiment of the present disclosure.

Having performed the analysis described above, the main reason for the abovementioned deficiency in the existing technique is that a fixed trigger point threshold is used; thus, no account is taken of the fact that the amplitude of the respiration signal might vary significantly in different respiration periods. Based on this finding, the present disclosure provides a solution in accordance with the embodiments described herein as follows:

FIG. 2 is a flow chart for triggering MR data acquisition provided in an embodiment of the present disclosure, specifically having the following steps:

Step 201: detecting a respiration direction of a respiration signal of an acquisition subject.

Step 202: predicting in real time an expiration amplitude peak value of an expiration signal in the current respiration period, according to the respiration signal of the acquisition subject.

Step 203: when it is determined according to the respiration direction of the respiration signal that an expiration stage of the current respiration period is starting, calculating in real time or periodically the product of the current expiration amplitude peak value and a preset coefficient to obtain a trigger point threshold of the current respiration period, calculating the absolute value of the difference between the amplitude of the current expiration signal and the trigger point threshold of the current respiration period and, if the absolute value of the difference is less than a preset difference threshold, then triggering MR data acquisition.

The preset coefficient can be determined according to experience, etc., and is generally 80% as a non-limiting example.

In the above embodiment, the amplitude peak value of the expiration signal in the current respiration period is predicted in real time according to the respiration signal of the acquisition subject, and the current trigger point threshold is determined according to the amplitude peak value, thus the trigger point threshold can vary as the amplitude of the respiration signal varies, thereby reducing the probability of missed, premature, or late triggering of MR data acquisition, and increasing the accuracy of triggering of MR data acquisition.

Figure 3:
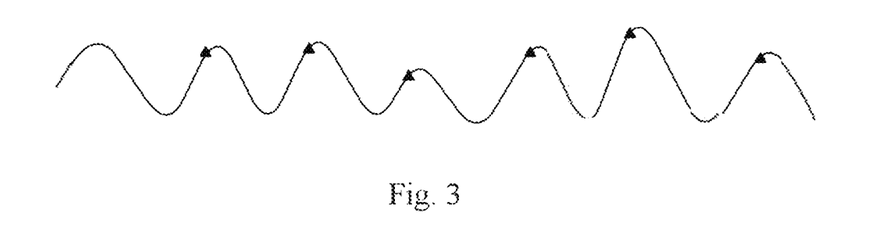
FIG. 3 is an exemplary diagram of MR data acquisition trigger points detected when the method provided in in accordance with an embodiment of the present disclosure is used.

FIG. 3 is an exemplary diagram of MR data acquisition trigger points detected when the method provided in an embodiment of the present disclosure is used; as can be seen, when the embodiment in accordance with the present disclosure is used, no matter how the amplitude of the respiration signal varies in different respiration periods, the trigger point can always be detected accurately.

In view of the fact that RF pulses or gradient pulses in the MR data acquisition process will cause interference to respiration signals, in order to reduce or eliminate this interference, a previous respiration signal that did not suffer interference can be used to predict a subsequent respiration signal.

Figure 4:
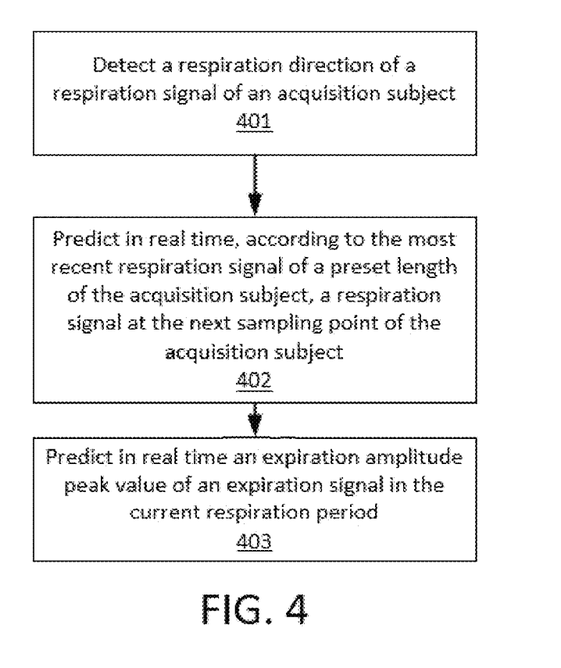
FIG. 4 is a flow chart for triggering MR data acquisition provided in another embodiment of the present disclosure.

FIG. 4 is a flow chart for triggering MR data acquisition provided in another embodiment of the present disclosure, specifically having the following steps:

Step 401: detecting a respiration direction of a respiration signal of an acquisition subject.

Step 402: predicting in real time, according to the most recent respiration signal of a preset length of the acquisition subject, a respiration signal at the next sampling point of the acquisition subject;

Step 403: predicting in real time an expiration amplitude peak value of an expiration signal in the current respiration period according to the respiration signal predicted in real time in step 402.

Step 404: when it is determined according to the respiration direction of the respiration signal that an expiration stage of the current respiration period is starting, calculating in real time or periodically the product of the current expiration amplitude peak value and a preset coefficient to obtain a trigger point threshold of the current respiration period, calculating the absolute value of the difference between the amplitude of the current expiration signal and the trigger point threshold of the current respiration period and, if the absolute value of the difference is less than a preset difference threshold, then triggering MR data acquisition.

In the above embodiment, before performing expiration signal amplitude peak value prediction for a respiration signal, a previous respiration signal is first used to predict a subsequent respiration signal, thereby reducing interference caused to respiration signals by RF pulses or gradient pulses in the process of MR data acquisition, and thereby further increasing the accuracy of triggering of MR data acquisition.

Figure 5:
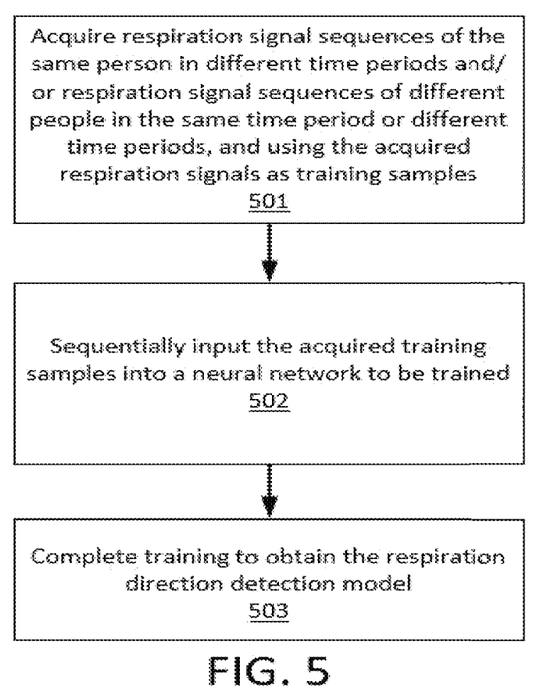
FIG. 5 is a flow chart for establishing a respiration direction detection model provided in an embodiment of the present disclosure.

In an actual application of the present disclosure, in order to detect a respiration direction of a respiration signal of the acquisition subject, a respiration direction detection model can be established in advance; FIG. 5 shows a flow chart for establishing a respiration direction detection model provided in an embodiment of the present disclosure, specifically having the following steps:

Step 501: acquiring respiration signal sequences of the same person in different time periods and/or respiration signal sequences of different people in the same time period or different time periods, and using the acquired respiration signals as training samples.

The respiration signals are represented by the amplitudes of respiration signals at various sampling points.

The acquisition of training samples may be performed in an environment free of human interference, e.g.: it is preferable that there is no interference from RF pulses and gradient pulses, etc.

Step 502: sequentially inputting the acquired training samples into a neural network to be trained; an output of the neural network is a correspondence between a respiration direction and amplitude variation of the currently inputted respiration signal, e.g.: rising amplitude stage: aspiration, falling amplitude stage: expiration, or: rising amplitude stage: expiration, falling amplitude stage: aspiration.

The greater the length of the input signal of the neural network, the more accurate the respiration direction detection model finally obtained will be.

Step 503: completing training to obtain the respiration direction detection model.

One respiration period comprises: an aspiration stage and an expiration stage. Two scenarios exist, depending on the way in which the original respiration signal acquired is processed:

In a first scenario, the rising amplitude stage in each respiration period is an aspiration stage, and the falling amplitude stage is an expiration stage.

Figure 6:
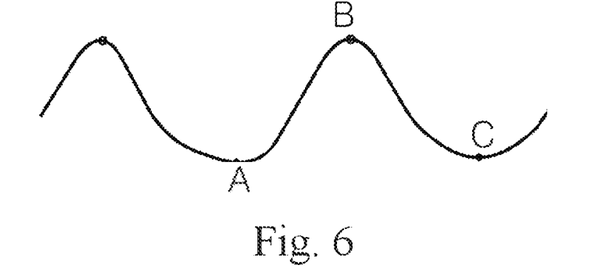
FIG. 6 is an exemplary diagram of a respiration signal in which a rising amplitude stage in each respiration period is an aspiration stage, and a falling amplitude stage is an expiration stage.

As shown in FIG. 6, in each respiration period the rising amplitude stage represents aspiration, and the falling amplitude stage represents expiration. For example, segment AB in FIG. 6 is a rising amplitude stage, i.e. an aspiration stage; segment BC is a falling amplitude stage, i.e. an expiration stage. Thus, when a respiration signal of a rising amplitude stage is inputted into the neural network to be trained, the corresponding output is: rising amplitude stage: aspiration (this can be represented by 10); and when a respiration signal of a falling amplitude stage is inputted into the neural network to be trained, the corresponding output is: falling amplitude stage: expiration (this can be represented by 01). Thus, in the course of training, the neural network will learn that: when the amplitude of the respiration signal is rising, this represents aspiration, and the output is 10; when the amplitude of the respiration signal is falling, this represents expiration, and the output is 01.

In a second scenario, the rising amplitude stage in each respiration period is an expiration stage, and the falling amplitude stage is an aspiration stage.

Figure 7:
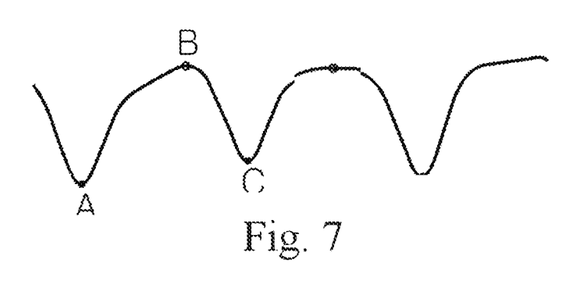
FIG. 7 is an exemplary diagram of a respiration signal in which a rising amplitude stage in each respiration period is an expiration stage, and a falling amplitude stage is an aspiration stage.

As shown in FIG. 7, in each respiration period, the rising amplitude stage represents expiration, and the falling amplitude stage represents aspiration. For example, segment AB in FIG. 7 is a rising amplitude stage, i.e. an expiration stage; segment BC is a falling amplitude stage, i.e. an aspiration stage. Thus, when a respiration signal of a rising amplitude stage is inputted into the neural network to be trained, the corresponding output is: rising amplitude stage: expiration (this can be represented by 11); and when a respiration signal of a falling amplitude stage is inputted into the neural network to be trained, the corresponding output is: falling amplitude stage: aspiration (this can be represented by 00). Thus, in the course of training, the neural network will learn that: when the amplitude of the respiration signal is rising, this represents expiration, and the output is 11; when the amplitude of the respiration signal is falling, this represents aspiration, and the output is 00.

When the respiration direction detection model is used, first a respiration signal segment of a patient is acquired, and this respiration signal segment is inputted into the respiration direction detection model; based on the output of the model, it is then possible to learn whether the rising stage and falling stage of the respiration signal in each respiration period correspond to aspiration or expiration, respectively.

After judging whether the rising stage and falling stage of the respiration signal in each respiration period correspond to aspiration or expiration, respectively, according to the initially acquired respiration signal segment, this result can be used directly to determine the respiration direction of the respiration signal of the patient in each respiration period. Specifically, if it is learned based on the output of the respiration direction detection model previously that a rising amplitude stage is expiration and a falling amplitude stage is aspiration, then after subsequently acquiring a respiration signal of the patient, the amplitude variation of the respiration signal of the patient is detected in real time, and if the amplitude is rising, this represents expiration, whereas if the amplitude is falling, this represents aspiration.

Figure 8:
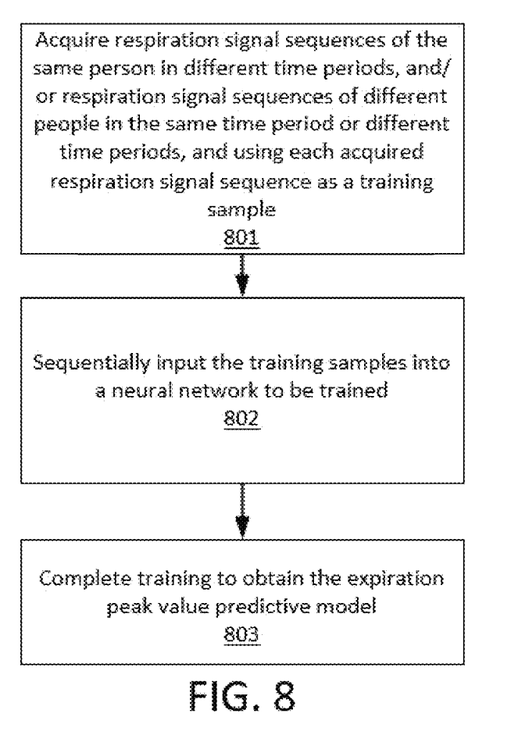
FIG. 8 is a flow chart for establishing an expiration peak value predictive model provided in an embodiment of the present disclosure.

In an actual application of the present disclosure, to predict the amplitude peak value of a respiration signal in the current respiration period, an expiration peak value predictive model can be established in advance; FIG. 8 shows a flow chart for establishing an expiration peak value predictive model provided in an embodiment of the present disclosure, specifically having the following steps:

Step 801: acquiring respiration signal sequences of the same person in different time periods, and/or respiration signal sequences of different people in the same time period or different time periods, and using each acquired respiration signal sequence as a training sample.

If a falling amplitude stage is expiration and a rising amplitude stage is aspiration in the original respiration signal sequence acquired, then it will be necessary to first of all subject the original respiration signal to processing, e.g.: multiply the amplitude of the original respiration signal sequence by −1, so that a rising amplitude stage is expiration and a falling amplitude stage is aspiration in the processed respiration signal sequence, and the processed respiration signal sequence is used as a training sample.

Step 802: sequentially inputting the training samples into a neural network to be trained, an output of the neural network being: an expiration amplitude peak value of the respiration period where the currently inputted respiration signal is situated.

Step 803: completing training to obtain the expiration peak value predictive model.

In the course of training the expiration peak value predictive model, the neural network will continuously learn the relationship between amplitude variation of the inputted respiration signal and the outputted expiration amplitude peak value.

Because the expiration peak value predictive model predicts the expiration amplitude peak value, a precondition for setting the model is that a rising amplitude stage of the respiration signal is expiration. Thus, when the expiration peak value predictive model is used, it is a requirement that the respiration direction of the inputted respiration signal should be a rising amplitude stage is expiration. Thus, if the output of the respiration direction predictive model is a rising amplitude stage is aspiration, then before the acquired original respiration signal of the patient is inputted into the expiration peak value predictive model, the original respiration signal should first be processed, e.g.: by the amplitude of the original respiration signal is multiplied by −1, so that a rising amplitude stage of the processed respiration signal is expiration; and the processed respiration signal is then inputted into the expiration peak value predictive model to perform expiration peak value prediction.

In an actual application, a trigger judgment time interval is set in advance; when it is detected that the respiration direction of the respiration signal currently inputted into the expiration peak value predictive model is the start of an expiration stage (i.e. switching from aspiration to expiration), the product of the expiration amplitude peak value outputted by the expiration peak value predictive model and a preset coefficient begins to be calculated at intervals of one trigger judgment time interval to obtain a trigger point threshold of the current respiration period; the absolute value of the difference between the amplitude of the current expiration signal and the trigger point threshold of the current respiration period is then calculated, and if the absolute value of the difference is less than a preset difference threshold, then MR data acquisition is triggered.

Figure 9:
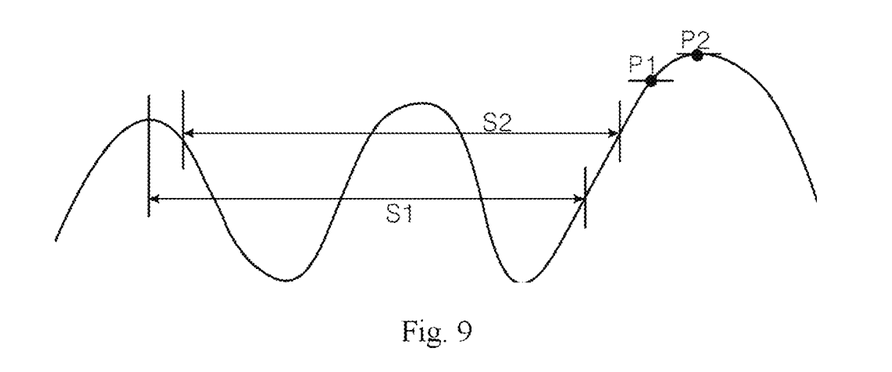
FIG. 9 is an exemplary diagram of using the technique provided in an embodiment of the present disclosure to perform expiration peak value prediction.

FIG. 9 is a real example of using the technique provided in an embodiment of the present disclosure to perform expiration peak value prediction. As shown in FIG. 9, S1 is a respiration signal segment inputted into the expiration peak value predictive model, and the expiration amplitude peak value predicted at this time is P1; at this time, $d1=|S1-P1*\alpha|$ is calculated, and $d1>dT$, wherein $\alpha$ is the preset coefficient and dT is the preset difference threshold, so MR data acquisition is not triggered; S2 is a respiration signal segment subsequently inputted into the expiration peak value predictive model, and the expiration amplitude peak value predicted at this time is P2; at this time, $d2=|S2-P2*\alpha|$ is calculated, and $d2<dT$, so MR data acquisition is triggered.

Figure 10:
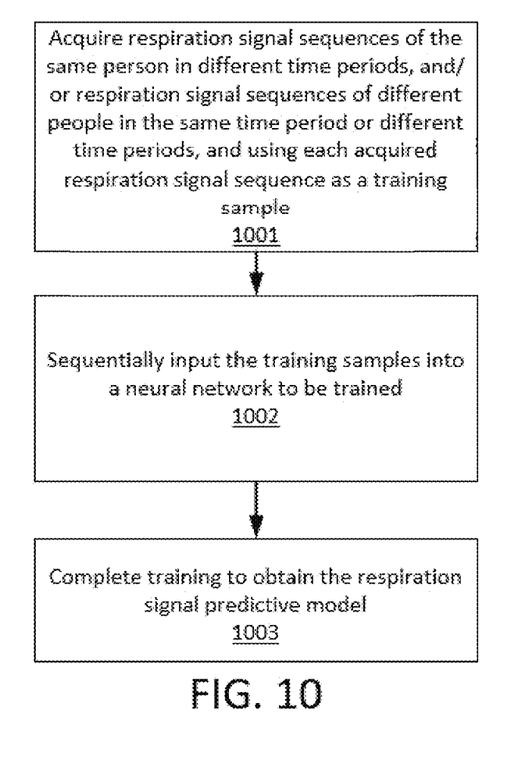
FIG. 10 is a flow chart for establishing a respiration signal predictive model provided in an embodiment of the present disclosure.

In an actual application of the present disclosure, to use a previous respiration signal that did not suffer interference to predict a subsequent respiration signal, a respiration signal predictive model can be established in advance; FIG. 10 is a flow chart for establishing a respiration signal predictive model provided in an embodiment of the present disclosure, specifically having the following steps:

Step 1001: acquiring respiration signal sequences of the same person in different time periods, and/or respiration signal sequences of different people in the same time period or different time periods, and using each acquired respiration signal sequence as a training sample.

If a falling amplitude stage is expiration and a rising amplitude stage is aspiration in the original respiration signal sequence acquired, then it will be necessary to first of all subject the original respiration signal sequence to processing, e.g.: multiply the amplitude of the original respiration signal sequence by −1, so that a rising amplitude stage is expiration and a falling amplitude stage is aspiration in the processed respiration signal sequence, and the processed respiration signal sequence is used as a training sample.

Step 1002: sequentially inputting the acquired training samples into a neural network to be trained, an output of the neural network being: a respiration signal obtained by delaying the inputted respiration signals by one sampling point.

For example: if the input signals of the neural network are: respiration signals $x(t_1), x(t_2), \ldots, x(t_k)$ at time points $t_1, t_2, \ldots, t_k$, then the output of the neural network is a respiration signal $x(t_{k+1})$ for time point $x(t_{k+1})$.

Step 1003: completing training to obtain the respiration signal predictive model.

In the course of training the respiration signal predictive model, the neural network will continuously learn the relationship between the inputted respiration signals and the outputted respiration signal, and finally establish an association between the inputted respiration signals (i.e. previous respiration signals $x(t_1), x(t_2), \ldots, x(t_k)$) and the outputted respiration signal (i.e. subsequent respiration signal $x(t_{k+1})$): $x(t_{k+1})=f(x(t_1), x(t_2), \ldots, x(t_k))$.

Because the respiration signal outputted by the respiration signal predictive model needs to be inputted into the expiration peak value predictive model, which requires the respiration direction of the inputted respiration signal to be such that a rising amplitude stage is expiration, the direction of the respiration signal outputted by the respiration signal predictive model is preferably also such that a rising amplitude stage is expiration. Thus, if the output of the respiration direction predictive model is: a rising amplitude stage is aspiration, then before the acquired original respiration signal sequence of the patient is inputted into the respiration signal predictive model, the original respiration signal sequence should first be processed, e.g.: the amplitude of the original respiration signal sequence is multiplied by −1, so that a rising amplitude stage of the processed respiration signal sequence is expiration; and the processed respiration signal sequence is then inputted into the respiration signal predictive model.

Figure 11:
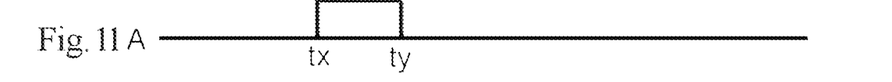
FIGS. 11A and 11B are exemplary diagrams of using the technique provided in an embodiment of the present disclosure to perform respiration signal prediction.

FIGS. 11A and 11B are examples of using the technique provided in an embodiment of the present disclosure to perform respiration signal prediction. FIG. 11A represents an RF pulse sequence, wherein the interval between time points tx and ty is the RF pulse transmission time. FIG. 11B represents a respiration signal sequence, and it can be seen that the respiration signal suffers serious interference during the RF pulse transmission time and for a period of time afterward, i.e. in the interval tx-tz in the figure. After the original respiration signal is inputted into the respiration signal predictive model, it can be seen that the outputted respiration signal in the interval tx-tz has become smooth, wherein point s1 is the respiration signal predicted using the original respiration signal in period t1, and point s2 is the respiration signal predicted using the original respiration signal in period t2; the lengths of t1 and t2 are the same, specifically the length of the inputted respiration signal of the respiration signal predictive model.

Figure 12:
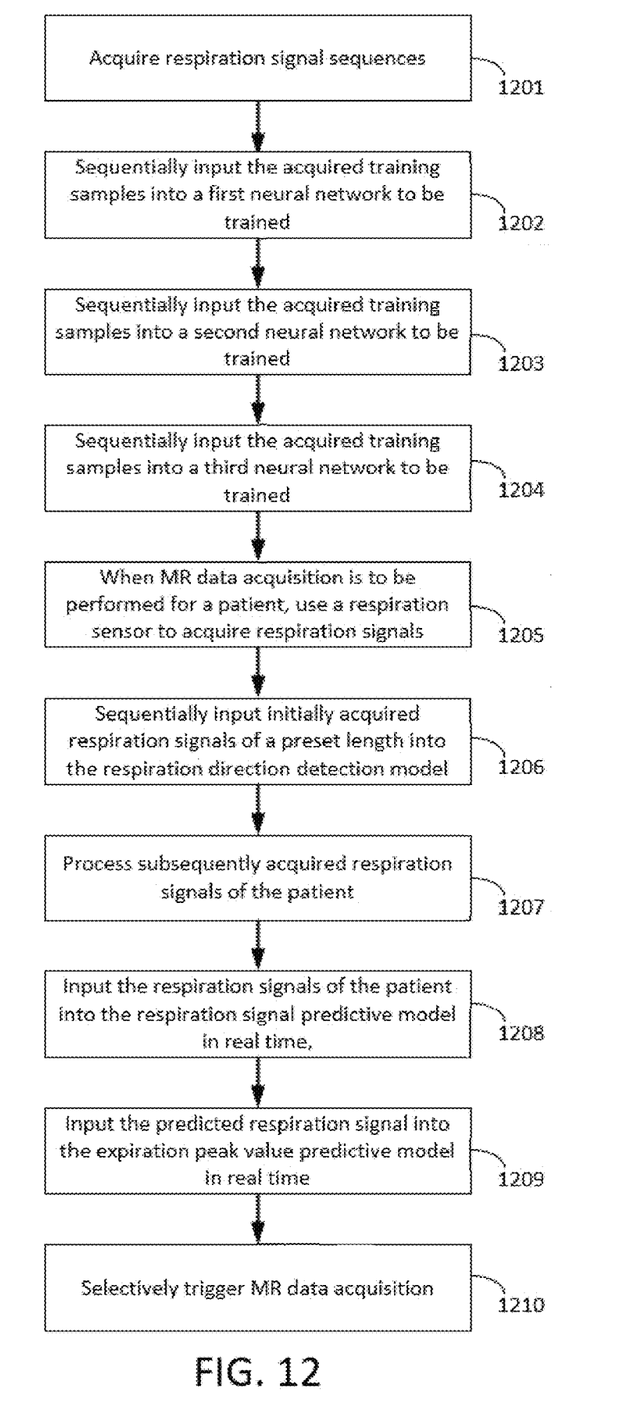
FIG. 12 is a flow chart for triggering MR data acquisition provided in another embodiment of the present disclosure.

FIG. 12 is a flow chart for triggering MR data acquisition provided in another embodiment of the present disclosure, specifically having the following steps:

Step 1201: acquiring respiration signal sequences of the same person in different time periods, and/or respiration signal sequences of different people in the same time period or different time periods, and using each acquired respiration signal sequence as a training sample.

The acquisition of training samples should be performed in an environment free of human interference, e.g.: there must be no interference from RF pulses and gradient pulses, etc.

Step 1202: sequentially inputting the acquired training samples into a first neural network to be trained, an output of the first neural network being a correspondence between a respiration direction and amplitude variation of the currently inputted respiration signal, e.g.: rising amplitude stage: aspiration, falling amplitude stage: expiration, or: rising amplitude stage: expiration, falling amplitude stage: aspiration; completing training to obtain a respiration direction detection model.

Step 1203: sequentially inputting the acquired training samples into a second neural network to be trained, an output of the second neural network being: a respiration signal obtained by delaying the inputted respiration signals by one sampling point; completing training to obtain a respiration signal predictive model.

The respiration direction of the training samples inputted into the second neural network should satisfy the following conditions: a rising amplitude stage is expiration; thus, before the acquired training samples are inputted into the second neural network, it is necessary to first input a portion of the training samples to the trained respiration direction detection model so as to detect whether the respiration direction of the training samples is such that a rising amplitude stage is expiration and, if it is not, all of the acquired training samples are processed, e.g.: the amplitudes of the acquired training samples are multiplied by −1, so that a rising amplitude stage of the processed training samples is expiration, and the processed training samples are then inputted into the second neural network.

Step 1204: sequentially inputting the training samples into a third neural network to be trained, an output of the third neural network being: an expiration amplitude peak value of the respiration period where the currently inputted respiration signal is situated; completing training to obtain an expiration peak value predictive model.

Similarly, the respiration direction of the training samples inputted into the third neural network should satisfy the following conditions: a rising amplitude stage is expiration; thus, before the acquired training samples are inputted into the third neural network, it is necessary to first input a portion of the training samples to the trained respiration direction detection model, so as to detect whether the respiration direction of the training samples is such that a rising amplitude stage is expiration and, if it is not, all of the acquired training samples are processed, e.g.: the amplitudes of the acquired training samples are multiplied by −1, so that a rising amplitude stage of the processed training samples is expiration, and the processed training samples are then inputted into the third neural network.

Step 1205: when MR data acquisition is to be performed for a patient, a respiration sensor is used to acquire respiration signals of the patient.

Step 1206: sequentially inputting initially acquired respiration signals of a preset length into the respiration direction detection model, the output of the model being a correspondence between the respiration direction and amplitude variation of the inputted respiration signals.

After the correspondence between the respiration direction and amplitude variation of the respiration signals has been judged according to the initially acquired respiration signals of the preset length, this result can be used directly to determine the respiration direction in each respiration period for subsequent respiration signals.

Step 1207: if it is determined in step 1206 that a falling amplitude stage of the respiration signals is expiration, then all subsequently acquired respiration signals of the patient are processed by having their amplitudes multiplied by −1, so that the respiration direction is changed such that a rising amplitude stage is expiration.

Step 1208: inputting the respiration signals of the patient into the respiration signal predictive model in real time, to obtain a predicted respiration signal.

Step 1209: inputting the predicted respiration signal into the expiration peak value predictive model in real time, to obtain a predicted expiration amplitude peak value of the current respiration period.

Step 1210: if the respiration signal currently inputted into the expiration peak value predictive model is in a rising amplitude stage, i.e. in an expiration stage, then at intervals of one trigger judgment time interval, the expiration amplitude peak value currently outputted by the expiration peak value predictive model is multiplied by a preset coefficient to obtain a current trigger point threshold, the absolute value of the difference between the amplitude of the respiration signal currently inputted into the expiration peak value predictive model and the current trigger point threshold is calculated, and if the absolute value of the difference is less than a preset difference threshold, then MR data acquisition is triggered.

Since the trigger point threshold is obtained by multiplying the expiration amplitude peak value by the preset coefficient, the size of the preset coefficient will also affect the accuracy of triggering of MR data acquisition. In an embodiment of the present disclosure, a solution for selecting the optimal preset coefficient is provided:

Different preset coefficients are used to calculate trigger point thresholds for the same respiration signal, and corresponding MR data acquisitions are carried out; finally, MR images corresponding to different preset coefficients are compared, and the preset coefficient corresponding to the best-quality MR image is then the optimal preset coefficient.

The neural networks mentioned in embodiments of the present disclosure may be any suitable type of neural network such as for instance TCN (Temporal Convolutional Networks), RNN (Recurrent Neural Networks) or LSTM (Long-Short-Term-Memory) neural networks, etc.

When an existing technique and the technique of the present disclosure are applied in the same MR data acquisition scenario, it is found that the triggering error is reduced by more than 40% in accordance with an embodiment of the present disclosure as compared with the existing technique. Moreover, in the technique in accordance with an embodiment of the present disclosure, the error will get smaller and smaller as the respiration motion trace approaches the end of expiration.

Figure 13:
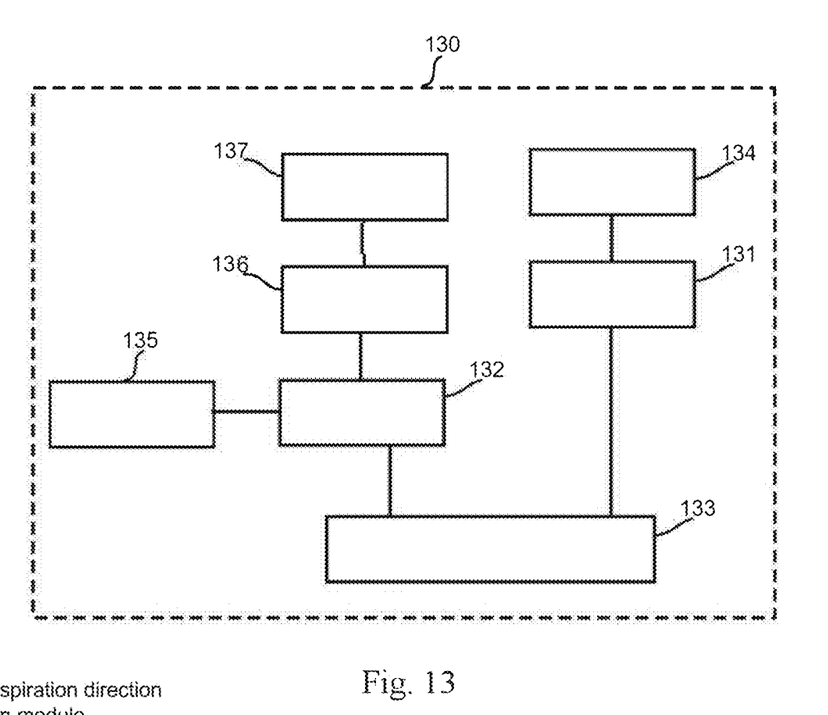
FIG. 13 is a structural schematic diagram of an apparatus for triggering MR data acquisition provided in an embodiment of the present disclosure.

FIG. 13 is a structural schematic diagram of an apparatus for triggering MR data acquisition provided in an embodiment of the present disclosure, the apparatus mainly comprising:

- a respiration direction detection module 131 (e.g. processing circuitry and/or processing circuitry configured to execute machine-readable instructions to perform specific tasks), for detecting a respiration direction of a respiration signal of an acquisition subject;
- an expiration peak value prediction module 132 (e.g. processing circuitry and/or processing circuitry configured to execute machine-readable instructions to perform specific tasks), for predicting in real time an expiration amplitude peak value of an expiration signal in the current respiration period, according to the respiration signal of the acquisition subject;
- a triggering detection module 133 (e.g. processing circuitry and/or processing circuitry configured to execute machine-readable instructions to perform specific tasks), for calculating in real time or periodically the product of the current expiration amplitude peak value predicted by the expiration peak value prediction module 132 and a preset coefficient, when it is determined according to the respiration direction of the respiration signal detected by the respiration direction detection module 131 that an expiration stage of the current respiration period is starting, to obtain a trigger point threshold of the current respiration period, calculating the absolute value of the difference between the amplitude of the current expiration signal and the trigger point threshold of the current respiration period, and if the absolute value of the difference is less than a preset difference threshold, then triggering MR data acquisition.

In an actual application, the apparatus 130 further comprises: a respiration direction detection model establishing module 134 (e.g. processing circuitry and/or processing circuitry configured to execute machine-readable instructions to perform specific tasks), for acquiring respiration signals of the same person in different time periods, and/or respiration signals of different people in the same time period or different time periods, and using the acquired respiration signals as training samples; sequentially inputting the acquired training samples into a first neural network to be trained, an output of the first neural network being a correspondence between a respiration direction and amplitude variation of the currently inputted respiration signal; and completing training to obtain a respiration direction detection model;

- moreover, the respiration direction detection module 131 is specifically configured to input the respiration signal of the acquisition subject into the respiration direction detection model established by the respiration direction detection model establishing module 134, and determine, according to the output of the model, a correspondence between a respiration direction and amplitude variation of the respiration signal of the acquisition subject in each respiration period.

In an actual application, the apparatus 130 further comprises: an expiration peak value predictive model establishing module 135 (e.g. processing circuitry and/or processing circuitry configured to execute machine-readable instructions to perform specific tasks), for acquiring respiration signals of the same person in different time periods, and/or respiration signals of different people in the same time period or different time periods, and using the acquired respiration signals as training samples; sequentially inputting the training samples into a third neural network to be trained, an output of the third neural network being: an expiration amplitude peak value of the respiration period where the currently inputted respiration signal is situated; and completing training to obtain an expiration peak value predictive model, wherein a rising amplitude stage of the respiration signal in each respiration period of the training sample is expiration;

- moreover, the expiration peak value prediction module 132 is configured to input the respiration signal of the acquisition subject into the expiration peak value predictive model established by the expiration peak value predictive model establishing module 135, the output of the model being an expiration amplitude peak value of the respiration period where the currently inputted respiration signal is situated, wherein the respiration signal of the acquisition subject satisfies: a rising amplitude stage of the respiration signal in each respiration period is expiration.

The apparatus 130 further comprises: a respiration signal prediction module 136 (e.g. processing circuitry and/or processing circuitry configured to execute machine-readable instructions to perform specific tasks), for predicting in real time, according to the most recent respiration signal of a preset length of the acquisition subject, a respiration signal at the next sampling point of the acquisition subject;

- moreover, the expiration peak value prediction module 132 is configured to predict in real time an expiration amplitude peak value of an expiration signal in the current respiration period, according to the respiration signal predicted in real time by the respiration signal prediction module 136.

The apparatus 130 further comprises: a respiration signal predictive model establishing module 137 (e.g. processing circuitry and/or processing circuitry configured to execute machine-readable instructions to perform specific tasks), for acquiring respiration signals of the same person in different time periods, and/or respiration signals of different people in the same time period or different time periods, and using the acquired respiration signals as training samples; sequentially inputting the training samples into a second neural network to be trained, an output of the second neural network being: a respiration signal at the next sampling point of the currently inputted respiration signal; and completing training to obtain a respiration signal predictive model, wherein a rising amplitude stage of the respiration signal in each respiration period of the training sample is expiration;

- moreover, the respiration signal prediction module 136 is configured to input the respiration signal of the acquisition subject into the respiration signal predictive model established by the respiration signal predictive model establishing module 137, the output of the model being a respiration signal at the next sampling point of the currently inputted respiration signal, wherein the respiration signal of the acquisition subject satisfies: a rising amplitude stage of the respiration signal in each respiration period is expiration.

Figure 14:
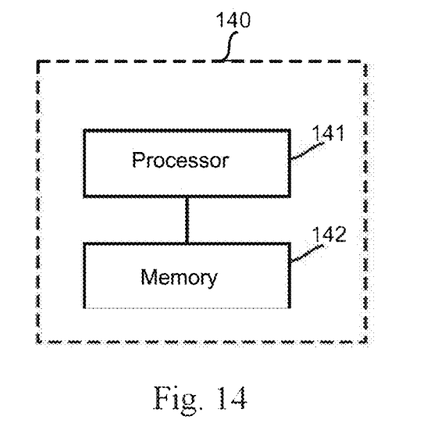
FIG. 14 is a structural schematic diagram of an apparatus for triggering MR data acquisition provided in another embodiment of the present disclosure.

FIG. 14 is a structural schematic diagram of an apparatus 140 for triggering MR data acquisition provided in an embodiment of the present disclosure, the apparatus mainly comprising: a processor 141 and a memory 142, wherein:

an application program executable by the processor 141 is stored in the memory 142, and configured to cause the processor 141 to perform a step of the flow chart, method, or technique as discussed herein for triggering MR data acquisition such as those described in steps 201-203, steps 401-403, steps 501-503, steps 801-803, steps 1001-1003, steps 1201-1210, etc.

An embodiment of the present disclosure also provides a readable storage medium, having a computer program stored thereon; when executed by a processor, the computer program realizes a step of the method for triggering MR data acquisition as described for instance in steps 201-203, steps 401-403, steps 501-503, steps 801-803, steps 1001-1003, steps 1201-1210, etc.

A machine-readable instruction is stored on the readable storage medium; the machine-readable instruction, when executed by a processor, causes the processor to perform any one of the methods described above. A system or apparatus equipped with a readable storage medium may be provided; software program code realizing a function of any one of the embodiments above is stored on the readable storage medium, and a computer or processor of the system or apparatus is caused to read and execute a machine-readable instruction stored in the readable storage medium.

In such a situation, program code read from the readable storage medium can itself realize a function of any one of the embodiments above, hence machine-readable code and the readable storage medium storing the machine-readable code form part of the present disclosure.

Examples of readable storage media include any suitable type of non-transitory computer-readable medium such as floppy disks, hard disks, magneto-optical disks, optical disks (such as CD-ROM, CD-R, CD-RW, DVD-ROM, DVD-RAM, DVD-RW, DVD+RW), magnetic tapes, non-volatile memory cards and ROM, etc. Optionally, program code may be downloaded from a server computer or a cloud via a communication network.

Those skilled in the art should understand that various changes in form and amendments may be made to the embodiments disclosed above without deviating from the substance of the disclosure. Thus, the scope of protection of the present disclosure shall be defined by the attached claims.

Further, not all of the steps and modules in the flows and system structure diagrams above are necessary; certain steps or modules may be omitted according to actual requirements. The order in which steps are executed is not fixed, but may be adjusted as required. The apparatus structures described in the embodiments above may be physical structures, and may also be logical structures, i.e. some modules might be realized by the same physical entity, or some modules might be realized by multiple physical entities, or realized jointly by certain components in multiple independent devices.

The present disclosure has been displayed and explained in detail above by means of the accompanying drawings and preferred embodiments, but the present disclosure is not limited to these disclosed embodiments. Based on the embodiments described above, those skilled in the art will know that further embodiments of the present disclosure, also falling within the scope of protection of the present disclosure, could be obtained by combining code checking means in different embodiments above.

What is claimed is:

1. A method for triggering magnetic resonance (MR) data acquisition, comprising:
    acquiring respiration signals of (i) a same person or different persons during (ii) a same time period or different time periods;
    sequentially inputting the acquired respiration signals as training samples to train a neural network such that an output of the neural network provides a correspondence between a respiration direction and amplitude variation of an inputted respiration signal to obtain a respiration direction detection model;
    detecting a respiration direction of a subsequent respiration signal associated with an acquisition subject by inputting the subsequent respiration signal associated with the acquisition subject into the respiration direction detection model, and determining, according to an output of the respiration direction detection model, a correspondence between a respiration direction and amplitude variation of the subsequent respiration signal associated with the acquisition subject for each respiration period;
    predicting, in real time, an amplitude peak value of an expiration signal in a current respiration period according to the subsequent respiration signal; and
    when it is determined according to the respiration direction of the subsequent respiration signal that an expiration stage of the current respiration period is starting:
        calculating, in real time or periodically, a product of a current expiration amplitude peak value and a predetermined coefficient to obtain a trigger point threshold of the current respiration period;
        calculating an absolute value of a difference between the amplitude of the current expiration signal and the trigger point threshold of the current respiration period; and
        when the absolute value of the difference is less than a predetermined difference threshold, triggering MR data acquisition.

2. The method as claimed in claim 1, further comprising:
    sequentially inputting the acquired respiration signals as training samples to train a further neural network such that an output of the further neural network provides an expiration amplitude peak value of a respiration period where an inputted respiration signal is located to obtain an expiration peak value predictive model,
    wherein a rising amplitude stage of a respiration signal in each respiration period of the training samples is expiration, and
    wherein predicting, in real time, the amplitude peak value associated with the expiration signal for the current respiration period comprises inputting the subsequent respiration signal associated with the acquisition subject into the expiration peak value predictive model, an output of the expiration peak value predictive model being an expiration amplitude peak value of the respiration period at which the subsequently inputted respiration signal is located, and
    wherein the subsequent respiration signal associated with the acquisition subject is such that a rising amplitude stage of the subsequent respiration signal during each respiration period is expiration.

3. The method as claimed in claim 1, the method further comprising:
after detecting the respiration direction of the subsequent respiration signal associated with an acquisition subject, but prior to predicting, in real time, the amplitude peak value associated with the expiration signal during the current respiration period:
predicting, in real time according to a most recent subsequent respiration signal of a predetermined length associated with the acquisition subject, a further subsequent respiration signal at a next sampling point;
wherein predicting in real time the amplitude peak value associated with the expiration signal for the current respiration period comprises predicting, in real time, the amplitude peak value associated with the expiration signal for the current respiration period according to the further subsequent respiration signal predicted in real time.

4. The method as claimed in claim 3, the method further comprising:
sequentially inputting the acquired respiration signals as training samples to train a further neural network such that an output of the further neural network provides the further respiration signal at the next sampling point of an inputted respiration signal to obtain a respiration signal predictive model,
wherein a rising amplitude stage of the respiration signal in each respiration period of the training samples is expiration;
wherein predicting in real time the further subsequent respiration signal at the next sampling point comprises inputting the subsequent respiration signal associated with the acquisition subject into the respiration signal predictive model to provide an output of the respiration signal predictive model as the further subsequent respiration signal at the next sampling point of the subsequently inputted respiration signal, and
wherein the subsequent respiration signal associated with the acquisition subject is such that a rising amplitude stage of the subsequent respiration signal in each respiration period is expiration.

5. The method as claimed in claim 1, wherein the neural network is one of a Temporal Convolutional Network (TCN), a Recurrent Neural Network (RNN), or a Long-Short-Term-Memory (LSTM) neural network.

6. An apparatus configured to trigger magnetic resonance (MR) data acquisition, comprising:
respiration direction detection circuitry configured to:
acquire respiration signals of (i) a same person or different persons during (ii) a same time period or different time periods;
sequentially input the acquired respiration signals as training samples to train a neural network such that an output of the neural network provides a correspondence between a respiration direction and amplitude variation of an inputted respiration signal to obtain a respiration direction detection model;
detect a respiration direction of a subsequent respiration signal associated with an acquisition subject by inputting the subsequent respiration signal associated with the acquisition subject into the respiration direction detection model, and determining, according to an output of the respiration direction detection model, a correspondence between a respiration direction and amplitude variation of the subsequent respiration signal associated with the acquisition subject for each respiration period;
expiration peak value prediction circuitry configured to predict, in real time, amplitude peak value of an expiration signal in a current respiration period according to the subsequent respiration signal; and
triggering detection circuitry configured to, when it is determined according to the respiration direction of the subsequent respiration signal detected by the respiration direction detection circuitry module that an expiration stage of the current respiration period is starting:
calculate, in real time or periodically, a product of a current expiration amplitude peak value and a predetermined coefficient to obtain a trigger point threshold of the current respiration period,
calculate an absolute value of a difference between the amplitude of the current expiration signal and the trigger point threshold of the current respiration period; and
when the absolute value of the difference is less than a predetermined difference threshold, triggering MR data acquisition.

7. The apparatus as claimed in claim 6, further comprising:
expiration peak value predictive model establishing circuitry configured to:
sequentially input the acquired respiration signals as training samples to train a further neural network such that an output of the further neural network provides an expiration amplitude peak value of a respiration period where an inputted respiration signal is located to obtain an expiration peak value predictive model,
wherein a rising amplitude stage of a respiration signal in each respiration period of the training samples is expiration; and
input the subsequent respiration signal associated with the acquisition subject into the expiration peak value predictive model, an output of the expiration peak value predictive model being expiration amplitude peak value of the respiration period at which the subsequently input respiration signal is located, and
wherein the subsequent respiration signal of the acquisition subject is such that a rising amplitude stage of the subsequent respiration signal during each respiration period is expiration.

8. The apparatus as claimed in claim 6, further comprising:
respiration signal prediction circuitry configured to:
predict, in real time according to a most recent subsequent respiration signal of a predetermined length associated with the acquisition subject, a further subsequent respiration signal at a next sampling point; and
predict, in real time, the amplitude peak value associated with the expiration signal for the current respiration period according to the further subsequent respiration signal predicted in real time.

9. The apparatus as claimed in claim 8, further comprising:
respiration signal predictive model establishing circuitry configured to:
sequentially input the acquired respiration signals as training samples to train a further neural network such that an output of the further neural network provides the further respiration signal at the next sampling point of an inputted respiration signal to obtain a respiration signal predictive model, wherein a rising amplitude stage of the respiration signal in each respiration period of the training samples is expiration; and input the subsequent respiration signal associated with the acquisition subject into the respiration signal predictive model to provide an output of the respiration signal predictive model as the further subsequent respiration signal at the next sampling point of the subsequently inputted respiration signal, and wherein the subsequent respiration signal of the acquisition subject is such that a rising amplitude stage of the subsequent respiration signal in each respiration period is expiration.

10. A readable storage medium, having a computer program stored thereon that, when executed by a processor, cause the processor to trigger magnetic resonance (MR) data acquisition by:

acquiring respiration signals of (i) a same person or different persons during (ii) a same time period or different time periods;

sequentially inputting the acquired respiration signals as training samples to train a neural network such that an output of the neural network provides a correspondence between a respiration direction and amplitude variation of an inputted respiration signal to obtain a respiration direction detection model;

detecting a respiration direction of a subsequent respiration signal associated with an acquisition subject by inputting the subsequent respiration signal associated with the acquisition subject into the respiration direction detection model, and determining, according to an output of the respiration direction detection model, a correspondence between a respiration direction and amplitude variation of the subsequent respiration signal associated with the acquisition subject for each respiration period;

predicting, in real time, an amplitude peak value of an expiration signal in a current respiration period according to the respiration signal; and when it is determined according to the respiration direction of the subsequent respiration signal that an expiration stage of the current respiration period is starting:

calculating, in real time or periodically, a product of a current expiration amplitude peak value and a predetermined coefficient to obtain a trigger point threshold of the current respiration period;

calculating an absolute value of a difference between the amplitude of the current expiration signal and the trigger point threshold of the current respiration period; and when the absolute value of the difference is less than a predetermined difference threshold, triggering MR data acquisition.

* * * * *